United States Patent
Naumann

(10) Patent No.: US 11,856,372 B2
(45) Date of Patent: Dec. 26, 2023

(54) HEARING DEVICE SYSTEM AND METHOD FOR OPERATING A HEARING DEVICE SYSTEM

(71) Applicant: Sivantos Pte. Ltd., Singapore (SG)

(72) Inventor: Frank Naumann, Bubenreuth (DE)

(73) Assignee: Sivantos Pte. Ltd., Singapore (SG)

( * ) Notice: Subject to any disclaimer, the term of this patent is extended or adjusted under 35 U.S.C. 154(b) by 11 days.

(21) Appl. No.: 17/591,827

(22) Filed: Feb. 3, 2022

(65) Prior Publication Data
US 2022/0248156 A1    Aug. 4, 2022

(30) Foreign Application Priority Data
Feb. 3, 2021    (DE) .................... 10 2021 200 984.0

(51) Int. Cl.
*H04R 25/00*    (2006.01)
*A61B 5/00*    (2006.01)

(52) U.S. Cl.
CPC ........... *H04R 25/70* (2013.01); *A61B 5/6803* (2013.01); *H04R 25/305* (2013.01); *H04R 25/65* (2013.01); *H04R 2225/0216* (2019.05)

(58) Field of Classification Search
CPC .................................................... H04R 25/305
USPC .......................................................... 381/312
See application file for complete search history.

(56) References Cited

U.S. PATENT DOCUMENTS

2007/0100090 A1*  5/2007  Klare ...................... A61L 27/26
                                                                525/454
2016/0113619 A1*  4/2016  Gold ......................... A61B 7/02
                                                                181/131
2017/0127193 A1    5/2017  Hunsung
2019/0033505 A1*  1/2019  Cross .................... A61B 5/0082
2019/0253793 A1    8/2019  Pedersen et al.
2020/0025732 A1    1/2020  Usher et al.
2020/0085326 A1    3/2020  Fransen et al.
2021/0298619 A1    9/2021  Stephenson et al.

FOREIGN PATENT DOCUMENTS

DE    102015219573 A1    4/2017
DE    102015221187 A1    5/2017
WO      2019232042 A1    12/2019

OTHER PUBLICATIONS

Translation of Aschoff et al. German Patent Publication No. 102015219573, Apr. 13, 2017 (Year: 2017).*

* cited by examiner

*Primary Examiner* — Katherine A Faley
(74) *Attorney, Agent, or Firm* — Laurence A. Greenberg; Werner H. Stemer; Ralph E. Locher

(57) ABSTRACT

A hearing device system has a photoplethysmography sensor to be worn in the auditory canal in an intended worn state and an earpiece which at least partly covers the photoplethysmography sensor toward the auditory canal in the intended worn state. Moreover, the hearing device system has a controller which is configured to use light captured by the photoplethysmography sensor to derive a comparison quantity of the earpiece characteristic for a transmission of the earpiece, for a wavelength range of the photoplethysmography sensor, to compare the comparison quantity with a specified first limit and to output an alert if the limit is traversed by the comparison quantity.

11 Claims, 2 Drawing Sheets

HEARING DEVICE SYSTEM AND METHOD FOR OPERATING A HEARING DEVICE SYSTEM

CROSS-REFERENCE TO RELATED APPLICATION

This application claims the priority, under 35 U.S.C. § 119, of German Patent Application DE 10 2021 200 984.0, filed Feb. 3, 2021; the prior application is herewith incorporated by reference in its entirety.

FIELD AND BACKGROUND OF THE INVENTION

The invention relates to a hearing device system. Moreover, the invention relates to a method for operating such a hearing device system.

Hearing devices are typically used to output an audio signal to the sense of hearing of the wearer of this hearing device. The output takes place by means of an output transducer, usually acoustically via airborne sound by means of a loudspeaker (also referred to as a "receiver"). Such hearing devices are frequently used as so-called hearing aid equipment (also in short: hearing aids). For this purpose, the hearing devices normally comprise an acoustic input transducer (in particular a microphone) and a signal processor, which is configured to process the input signal (also: microphone signal) generated by the input transducer from the ambient sound with application of at least one typically user-specific stored signal processing algorithm in such a way that a hearing loss of the wearer of the hearing device is at least partially compensated for. In particular in the case of a hearing aid device, the output transducer can be, in addition to a loudspeaker, alternatively also a so-called bone vibrator or a cochlear implant, which are configured for mechanical or electrical coupling of the sound signal into the sense of hearing of the wearer. The term hearing devices also additionally includes in particular equipment such as, e.g., so-called tinnitus maskers, headsets, headphones, and the like.

In a manner comparable to the ever more widespread use of functions of so-called "wearables", for example in the form of fitness armbands, "smartwatches" and the like, which inter alia measure body functions (e.g., pulse, movement and the like) by means of sensors, the use of such functions is also starting to find its way into the field of hearing devices. By way of example, the intention is to measure body temperature, pulse or the like. Such an additional use of the hearing devices is also in the offering since, particularly in the case of hearing aid equipment, hearing devices are usually worn close to the body and frequently also worn over a comparatively long period of time, or even worn continuously.

SUMMARY OF THE INVENTION

The invention is based on the object of improving the capture of body functions by means of a hearing device.

This object is achieved according to the invention by a hearing device having the features of the independent hearing device claim. Moreover, this object is achieved according to the invention by a method having the features of the independent method claim. Advantageous embodiments and refinements of the invention, which are partially inventive as such, are represented in the dependent claims and the following description.

The hearing device system according to the invention has a photoplethysmography sensor which, in an intended worn state, should be worn in the auditory canal of the person using the hearing device system. Moreover, the hearing device system has an earpiece which at least partly covers the photoplethysmography sensor toward the auditory canal in the intended worn state. In particular, the earpiece serves, at least indirectly, to keep the photoplethysmography sensor in an intended worn position in the auditory canal. Moreover, the hearing device system has a controller which is configured to use a light captured (and preferably also emitted) by the photoplethysmography sensor to derive a comparison quantity characteristic for a transmission of the earpiece, for a wavelength range used by the photoplethysmography sensor. Moreover, the controller is configured to compare the comparison quantity with a specified first limit (value) and to output an alert if the first limit is crossed by the comparison quantity.

According to the method according to the invention, in order to operate the above-described hearing device—which thus has the photoplethysmography sensor to be worn in the auditory canal in an intended worn state and the earpiece which at least partly covers the photoplethysmography sensor toward the auditory canal in the intended worn state—light captured by the photoplethysmography sensor is used to derive the comparison quantity for the transmission of the earpiece, for a wavelength range of the photoplethysmography sensor; the comparison quantity is compared with a specified first limit; and an alert is output if the limit is traversed by the comparison quantity.

The hearing device system, specifically the controller thereof, is configured to carry out the method according to the invention, in particular independently. Accordingly, conversely, the method includes all measures performed by the controller, which are described here and below. Consequently, the hearing device system and the method accordingly share the features (in particular the method-related features) and the advantages emerging therefrom, which are described here and below.

Here and below, characteristic means that the comparison quantity contains quantitative information about the magnitude of the transmission such that the transmission can be read, at least indirectly, from the comparison variable. Hence, the comparison quantity specifies for example the transmission (in particular the transmission of the entire transmission route of the light of the photoplethysmography sensor) itself, or else alternatively the absorption which is complementary to the transmission. A comparison quantity may also be a quantity that is directly or indirectly proportional to the transmission to be indicated. Further, the comparison quantity may also be related in a nonlinear fashion, for example a logarithmic, exponential or polynomial (that is to say, quadratic, cubic, etc.) fashion, to the transmission to be indicated.

Both here and below, the term "traversing the limit" (in this case, traversing the first limit) should preferably always be understood in directionally independent fashion, within the meaning of the difference between the comparison quantity (or its changeover time) and the limit changing the sign. Depending on the definition of the comparison quantity ("true" transmission of absorption), traversing the respective limit can thus be positive (within the meaning of an overshoot, in which the comparison quantity becomes larger than the limit) or negative (within the meaning of an undershoot, in which the comparison quantity becomes smaller than the limit). Consequently, the alert is output, in particular, if the comparison quantity reflects the absorption and becomes greater than the first limit. Accordingly, conversely, the alert is preferably output if the comparison quantity reflects the transmission and drops below the first limit.

Since the measurement principle of the photoplethysmography sensor is based on irradiating the body tissue with the light from one or more specified wavelength ranges (or different bands in the near infrared range and/or visible wavelength range) and capturing reflected or transmitted radiation and drawing on the latter to determine tissue properties, in particular the current perfusion, the transmission of the earpiece clearly influences the evaluation and determination of the tissue properties. Therefore, the above-described first limit is preferably chosen (specified) in such a way that a sufficient amount of light is still received for the evaluation and determination of the tissue properties. Expressed differently, the first limit preferably specifies the boundary beyond which a reliable evaluation and determination of the tissue properties is no longer possible. Consequently, the determination and the comparison of the comparison quantity with the first limit advantageously informs the user of the hearing device system that the function of the photoplethysmography sensor is limited.

In a preferred embodiment, the controller is configured to compare the comparison quantity with a second limit (value) in addition to the first limit and to deduce a first type, in particular a first color type, of the earpiece on the basis of a relative position of the comparison quantity in relation to the second limit. This is advantageous, in particular, to the effect that earpieces with different colorations (that is to say different color types) are frequently available for hearing devices. However, even if the earpiece still is translucent, not all colorations are suitable for the reliable use (that is to say, use that supplies sufficiently accurate results) of the photoplethysmography sensor since at least a significant proportion of light is absorbed.

In an expedient development of the embodiment described above, the controller is configured to compare the comparison quantity with a third limit (value). In this case, the first limit is between the second and the third limit. In this case, the controller is configured, in particular, to deduce a second type, in particular a second color type, of the earpiece on the basis of a relative position of the comparison quantity in relation to the third limit. Thus, the controller is in particular configured to distinguish between a color type having a sufficiently high transmission and a color type having a transmission that is too low. In particular, this is advantageous in that different earpieces with different colorations (that is to say different color types), for example light, dark, transparent, opaque or the like, are often available for hearing devices. Should the controller detect a type, in particular a color type, of the earpiece that is unsuitable for the use of the photoplethysmography sensor, the controller is preferably configured to output a recommendation for a suitable type.

By way of example, the second limit (where the latter and hence also the comparison quantity represent the transmission itself) is above the first limit (that is to say, represents a higher value of the transmission itself than the value set by the first limit). In this case, the third limit is below the first limit in particular and consequently represents a transmission that is significantly too low.

Optionally, a plurality of second and/or third limits are also specified, on the basis of which it is possible to distinguish between, e.g., a plurality of colorations or else a plurality of earpieces from different manufacturers.

In an advantageous embodiment, the controller is configured to draw upon the first limit being traversed by the comparison quantity as an indication for dirtying of the earpiece and to output a request to clean or renew the earpiece with the alert.

In an advantageous combination of the detection of contamination with the above-described comparison with the second limit or else with the third limit, the controller is advantageously configured to deduce the contamination if only the first limit is exceeded, but not the second or third limit. In this context, a detection of the contamination is advantageously possible if the transmission of the color type of the earpiece which is unsuitable for the use of the photoplethysmography sensor is so low (expressed differently, if the absorption thereof is so high) that the distance of the first limit, from where the use of the photoplethysmography sensor is significantly influenced, to a transmission value usually reduced due to dirtying, is smaller than to the second or third limit assigned to the unsuitable color type. In this case, it is consequently not only such an unsuitable color type but also dirtying that leads to the output of an alert, preferably to a different output of an alert, assigned respectively.

In a preferred embodiment, the hearing device system has a hearing device (in particular a hearing aid), to which the photoplethysmography sensor is coupled. In particular, the photoplethysmography sensor is part of the hearing device. In this case, the controller is expediently configured to determine the comparison quantity following a replacement of the earpiece and/or following an activation of the hearing device, and preferably also to compare the comparison quantity with the limit or the respective limit. Optionally, the controller is configured to repeatedly determine the comparison quantity, even during running operation of the hearing device, and in particular also compare the comparison quantity to the limit or the respective limit.

In an advantageous embodiment, the first limit, and optionally also the second and/or the third limit, is chosen such that an influence of body tissue on the light emitted by the photoplethysmography sensor is taken into account. Expressed differently, the corresponding limit has already been chosen such the comparison quantity is determined following the irradiation of the body tissue. It is known that there is "attenuation" of the emitted light by the body tissue (in addition to that by the earpiece). Consequently, the first limit preferably specifies the amount of light needed to be captured, following the irradiation of the body of the user, for the proper, in particular reliable use of the photoplethysmography sensor. Accordingly, the second and/or third limit value—if present—specify the amount of light needed to be captured, following the irradiation of the body, in order to assign the respective color type to the earpiece.

Preferably, the first limit (in particular the second and the third limit as well) forms the ratio of the amount of light (intensity) to be received to the amount of light emitted. In particular, the first limit is at least 65 percent at a wavelength of the order of 860 (+/−20) nanometers.

In a further advantageous embodiment, the hearing device contains a main body to be worn behind the ear, the main body containing a signal processor and at least one microphone coupled therewith. Moreover, the hearing device in this case contains a loudspeaker which is to be worn in the auditory canal and which is coupled to the signal processor for signal transmission purposes. In particular, the hearing device is a behind-the-ear hearing aid (also referred to as "BTE") with an external loudspeaker (inter alia also referred to as "RIC" for "receiver in canal" or "RIC-BTE"). In this embodiment, the loudspeaker preferably carries the photoplethysmography sensor; in particular, the latter is integrated in the loudspeaker.

Particularly in the aforementioned case of the "RIC" hearing aid, the earpiece (which is in particular provided or suitable for use with the photoplethysmography sensor) is preferably formed as a flexible cover for the loudspeaker and formed from transparent, in particular non-colored material. By way of example, the earpiece—also referred to as an "ear dome" in this case—is formed from a silicone. By contrast, an earpiece unsuitable for use with the photoplethysmography sensor is formed by a colored material (in particular a darkly colored material), in particular silicone, for example.

The above-described controller of the hearing device system is optionally in the form of a non-programmable electronic circuit. Alternatively, the controller is formed by a microcontroller, in which the functionality for carrying out the above-described method according to the invention is implemented in the form of a software module.

In an optional embodiment, the controller is integrated in the signal processor of the hearing device. In an alternative embodiment or optionally in an additional embodiment as well (for example in order to be able to selectively adopt an energy saving mode for the hearing device), the controller is formed externally to the hearing device and implemented for example on a smartphone as an app (i.e., the aforementioned software module is implemented in this way). Consequently, particularly if an app is installed and at least during the use of the app, the smartphone constitutes a part of the hearing device system. In this case, the data (in particular the sensor signals) of the photoplethysmography sensor are transferred to the smartphone, preferably in wireless fashion, by means of a communications interface of the hearing device.

Other features which are considered as characteristic for the invention are set forth in the appended claims.

Although the invention is illustrated and described herein as embodied in a hearing device system and a method for operating a hearing device system, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Parts and variables corresponding to one another are always provided with the same reference signs in all figures.

Figure 1:
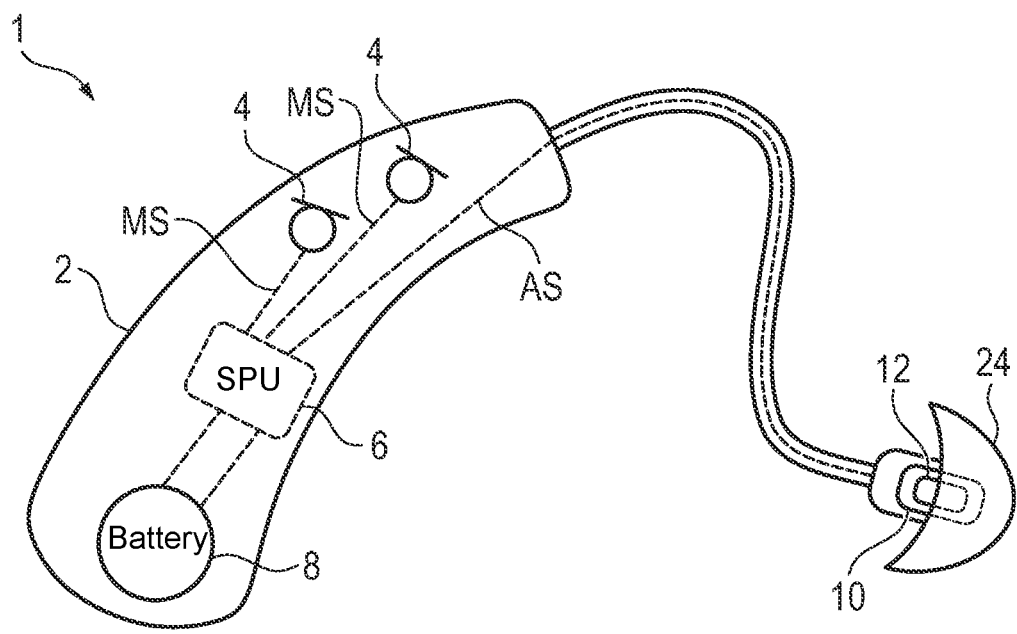
FIG. 1 is a schematic illustration of a hearing device system with a hearing device which has an external loudspeaker and a photoplethysmography sensor.

Referring now to the figures of the drawings in detail and first, particularly to FIG. 1 thereof, there is shown a hearing device in the form of hearing aid equipment, specifically hearing aid equipment to be worn behind the ear of a user (also referred to as hearing aid for short; denoted here as "BTE 1"). The BTE 1 contains a housing 2, in which electronic components of the BTE 1 are arranged. These electronic components are, for example, two microphones 4, a signal processor 6, and a battery module 8. The microphones 4 are used in the intended operation of the BTE 1 for receiving ambient sound and converting it into electrical input signals (also: "microphone signals MS"), which are processed (in particular filtered, amplified and/or damped depending on frequency, etc.) by the signal processor 6 (also referred to as "controller"). The processed input signals are subsequently output as output signals AS to a loudspeaker 10 which is arranged externally to the housing 2 and intended to be worn in the auditory canal 9, the loudspeaker converting said output signals into sound signals and transmitting these to the hearing of the user.

Figure 2:
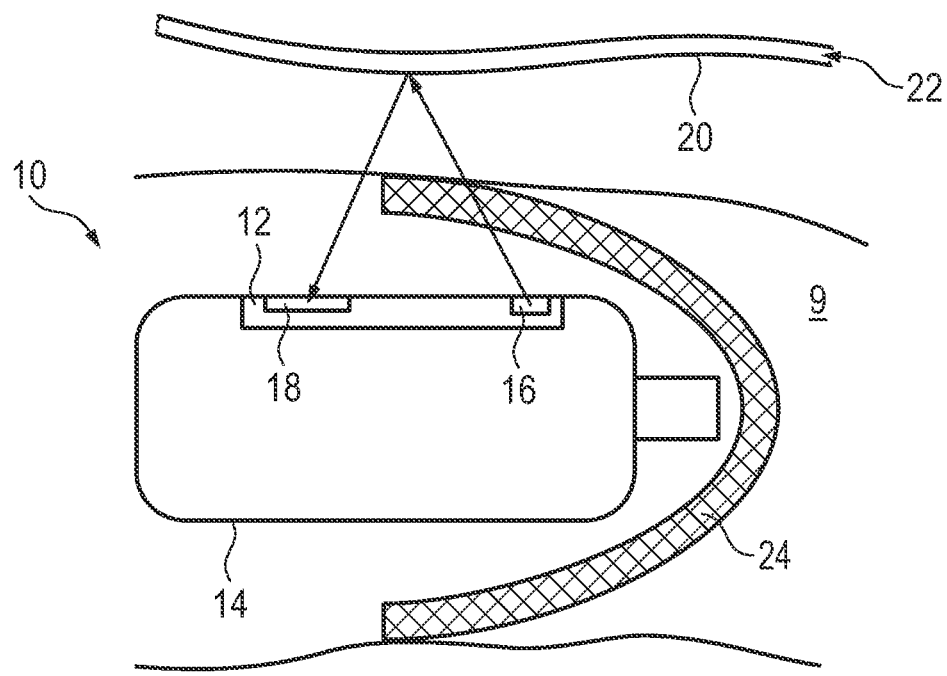
FIG. 2 is a schematic partial sectional view of the loudspeaker with the photoplethysmography sensor in the auditory canal of a user, in the intended worn state.

Moreover, the BTE 1 has a photoplethysmography sensor, "PPG sensor 12" for short, which is integrated in the loudspeaker 10, specifically inserted into its housing 14 (see FIG. 2), in the present exemplary embodiment. The PPG sensor 12 serves to determine, e.g., the pulse, optionally also the oxygen saturation, of the user of the BTE 1. To this end, the PPG sensor 12 contains a light source, an LED unit 16 in the present case, which is configured to output a plurality of frequency bands, but usually at least light in the near infrared range. Moreover, the PPG sensor 12 contains a light sensor 18, by means of which incident light is captured. During the intended use, the light sensor 18 captures radiation which is output by the LED unit 16 and reflected by body tissue, for example a vessel wall 20 of a blood vessel 22 of the user. By way of example, the pulse of the user can then be determined on the basis of the intensity profile captured in the process.

To keep the loudspeaker 10 in the auditory canal 9, the BTE 1 is moreover equipped with an earpiece, specifically formed here by a mushroom-like and flexible cover, which is also referred to as "dome 24" (or else: "sleeve"). As is evident from FIGS. 1 and 2, this dome 24 at least partly covers the PPG sensor 12. On account of the absorption inherent to the material of the dome 24 (that is to say a transmission of less than 100 percent), the light is thus already attenuated on its path between the LED unit 16 and the light sensor 18. Depending on the coloration of the dome 24, this attenuation is more or less pronounced. Usually, differently colored domes 24 are available for the BTE 1, usually a non-colored and a dark variant.

The BTE 1 also forms a "hearing device system" together with the currently applied dome 24.

Figure 3:
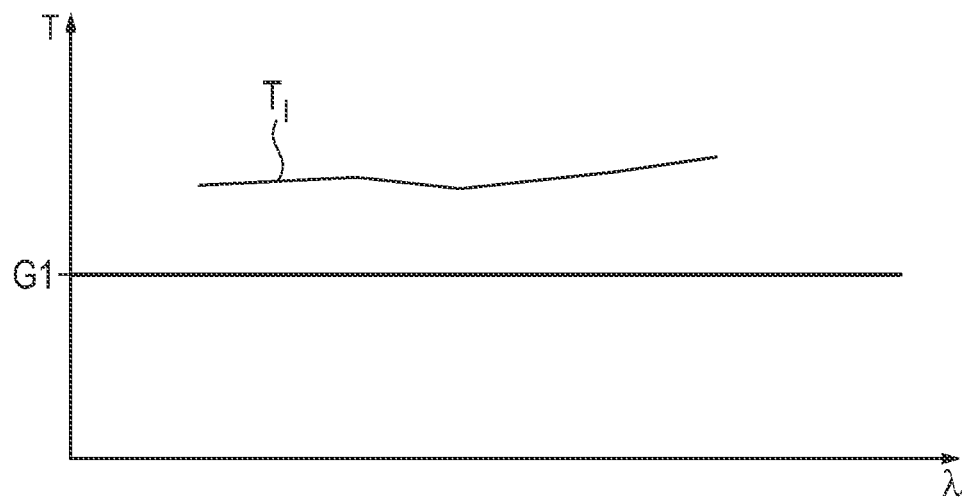
FIGS. 3 and 4 are graphs each showing a comparison quantity for a transmission of an earpiece determined in the intended worn state by means of the photoplethysmography sensor.

However, a specified intensity value received at least by means of the light sensor 18 is required for an intended use, specifically for reliable results, of the PPG sensor 12. Therefore, the signal processor 6 is configured to determine a comparison quantity, which is characteristic for the transmission of the dome 24, on the basis of the captured light (optionally for each emitted wavelength band or only in exemplary fashion for one band). In this context, this comparison quantity—referred to here as "actual transmission value TI"—is determined as a ratio of the captured intensity of the light to the intensity emitted by the LED unit 16. Consequently, this actual transmission value TI contains the attenuation both by the dome 24 and by the body tissue of the user. FIG. 3 shows a diagram in which the transmission T is plotted against the wavelength λ. In this case, the curve of the actual transmission value TI over the captured wavelength bands is illustrated in exemplary fashion.

Subsequently, the signal processor 6 compares the actual transmission value TI with a specified first limit G1 (see FIG. 3). This first limit G1 is chosen such that a function of the PPG sensor 12 below the first limit G1 is not reliable, that is to say the attenuation (absorption) by the dome 24 and the body tissue is too high. If the actual transmission value TI is above the first limit G1, as illustrated in FIG. 3, the signal processor 6 continues the intended operation. The signal processor 6 outputs an alert if the actual transmission value T1 undershoots the first limit G1.

Figure 4:
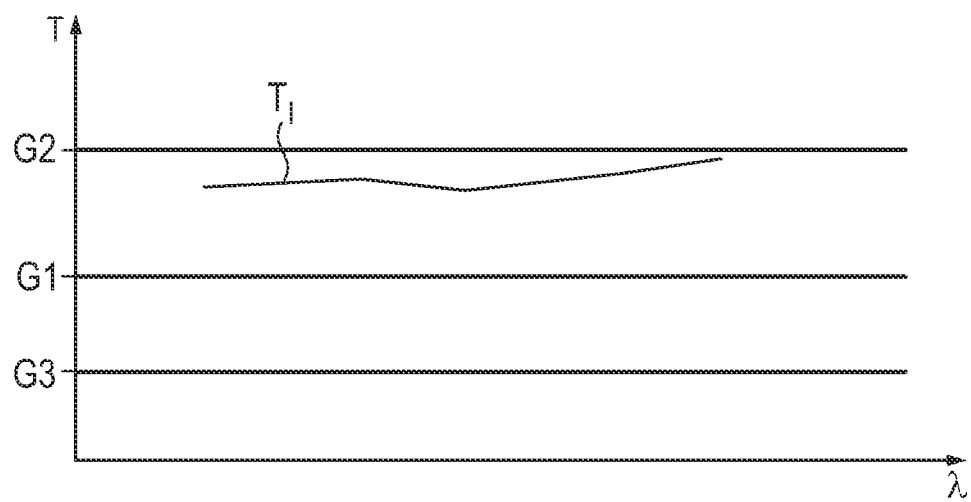

To be able to specify the alert in more detail, a second limit G2 and a third limit G3 are stored in the signal processor 6 in a further exemplary embodiment (see FIG. 4). In this case, the second limit G2 is above the first limit G1 and the third limit G3 is below the latter.

As a result, the signal processor 6 may also distinguish between different types, specifically different colors, specifically in this case a bright or colorless and a dark color, of the dome 24. If the actual transmission value T1 undershoots the first and the third limit G1 and G3, the signal processor 6 deduces that the dark color variant of the dome 24 is assembled. With the alert, the signal processor 6 outputs the instruction to assemble the non-colored variant of the dome 24.

If the actual transmission value T1 also traverses the second limit G2, the signal processor 6 deduces that the non-colored variant of the dome 24 is assembled.

Should the actual transmission value TI undershoot the first limit G1 but not the third limit G3, the signal processor 6 in a further exemplary embodiment deduces that the dome 24 is dirtied, for example because cerumen has been deposited on the dome 24. In this case, the signal processor 6 outputs the recommendation to clean or replace the dome 24 in addition to the alert.

In an exemplary embodiment not illustrated in any more detail, the aforementioned hearing device system moreover contains a smartphone on which a software application is implemented, the latter being configured and provided to evaluate the data from the PPG sensor 12. In this exemplary embodiment, this application is also configured and provided to carry out the "monitoring" of the transmission of the dome 24, which is carried out by the signal processor 6 in the foregoing text. In this case, the smartphone, specifically its microprocessor in conjunction with the application, thus represents a controller which determines the actual transmission value T1 and which compares the latter with the first limit G1 and optionally also with the second and third limits G2 and G3, and which optionally outputs the alert. In this case, the BTE 1 has a wireless interface, by means of which the data of the PPG sensor 12 are transmitted to the smartphone.

The subject matter of the invention is not restricted to the above-described exemplary embodiments. Rather, further embodiments of the invention can be derived by a person skilled in the art from the above description. In particular, the individual features of the invention described on the basis of the various exemplary embodiments and their design variants can also be combined with one another in another way.

The following is a summary list of reference numerals and the corresponding structure used in the above description of the invention:

1 BTE
2 Housing
4 Microphone
6 Signal processor
8 Battery module
9 Auditory canal
10 Loudspeaker
12 PPG sensor
14 Housing
16 LED unit
18 Light sensor
20 Vessel wall
22 Blood vessel
24 Dome
MS Microphone signal
AS Output signal
T Transmission
TI Actual transmission value
G1 First limit
G2 Second limit
G3 Third limit
λ Wavelength

The invention claimed is:

1. A hearing device system, comprising:
a photoplethysmography sensor to be worn in an auditory canal in an intended worn state;
an earpiece which at least partly covers said photoplethysmography sensor toward the auditory canal in the intended worn state;
a controller configured to use light captured by said photoplethysmography sensor to derive a comparison quantity of said earpiece being characteristic for a transmission through said earpiece, for a wavelength range of said photoplethysmography sensor, to compare the comparison quantity with a specified first limit and to output an alert if the specified first limit is traversed by the comparison quantity;
said controller configured to compare the comparison quantity with a second limit and to deduce a first type of said earpiece on a basis of a relative position of the comparison quantity in relation to the second limit; and
said controller configured to compare the comparison quantity with a third limit, the specified first limit being between the second limit and the third limit, and to deduce a second type of said earpiece on a basis of a relative position of the comparison quantity in relation to the third limit.

2. The hearing device system according to claim 1, wherein said controller is configured to draw upon whether the specified first limit has been crossed by the comparison quantity as an indication for dirtying of said earpiece and to output a request to clean or renew said earpiece with the alert.

3. The hearing device system according to claim 2, wherein said second limit is above said first limit and said third limit is below said first limit and said controller is configured to deduce dirtying if only the specified third limit is crossed and not the second limit or the first limit.

4. The hearing device system according to claim 1, wherein said controller is configured to determine the comparison quantity following a replacement of said earpiece and/or following an activation of the hearing device.

5. The hearing device system according to claim 1, wherein at least one of the specified first limit, the second limit or the third limit, is chosen such that an influence of body tissue on light emitted by said photoplethysmography sensor is taken into account.

6. The hearing device system according to claim 1, wherein the hearing device has a main body that is to be worn behind an ear, said main body containing said controller being a signal processor, at least one microphone coupled to said signal processor, and a loudspeaker which is to be worn in the auditory canal and coupled to said signal processor for signal transmission purposes, said loudspeaker carrying said photoplethysmography sensor.

7. The hearing device system according to claim 6, wherein said earpiece is configured as a flexible cover for said loudspeaker and is formed from a transparent material.

8. The hearing device system according to claim 7, wherein said transparent material is a non-colored material.

9. The hearing device system according to claim 1, wherein the first type of said earpiece is a first color type of said earpiece.

10. The hearing device system according to claim 1, wherein the second type of said earpiece is a second color type of said earpiece.

11. A method for operating a hearing device system having a photoplethysmography sensor to be worn in an auditory canal in an intended worn state and an earpiece covering the photoplethysmography sensor toward the auditory canal in the intended worn state, which comprises the steps of:
- using light captured by the photoplethysmography sensor to derive a comparison quantity characteristic for a transmission through the earpiece, for a wavelength range of the photoplethysmography sensor;
- comparing the comparison quantity with a specified first limit;
- outputting an alert if the specified first limit is traversed by the comparison quantity;
- comparing the comparison quantity with a second limit and deducing a first type of the earpiece on a basis of a relative position of the comparison quantity in relation to the second limit; and
- comparing the comparison quantity with a third limit, the specified first limit being between the second limit and the third limit, and deducing a second type of the earpiece on a basis of a relative position of the comparison quantity in relation to the third limit.

* * * * *